United States Patent [19]

Uster et al.

[11] Patent Number: 4,944,948

[45] Date of Patent: Jul. 31, 1990

[54] EGF/LIPOSOME GEL COMPOSITION AND METHOD

[75] Inventors: Paul S. Uster, Palo Alto; Robert M. Fielding, Redwood City; Francis J. Martin, San Francisco, all of Calif.

[73] Assignee: Liposome Technology, Inc., Menlo Park, Calif.

[21] Appl. No.: 315,392

[22] Filed: Feb. 24, 1989

[51] Int. Cl.⁵ .................................... A61K 37/22
[52] U.S. Cl. ................................ 424/450; 424/1.1; 264/4.3
[58] Field of Search ................ 424/450, 1.1; 264/4.3

[56] References Cited

U.S. PATENT DOCUMENTS 4,781,871 11/1988 West, III et al. ................ 424/450

OTHER PUBLICATIONS

Brown, G. L., et al., Ann. Surg. 208 (6) p. 788 (1988).
Mayhew, E., et al., Exp. Cell Res. 171 p. 195 (1987).
Buckley, A., et al., Proc. Natl. Acad. Sci. USA 82 p. 7340 (1985).

Primary Examiner—Ellis P. Robinson
Assistant Examiner—P. C. Prater
Attorney, Agent, or Firm—Peter J. Dehlinger

[57] ABSTRACT

A composition and method for treating a wound or surgical incision, by sustained-released delivery of epidermal growth factor (EGF). The composition includes a high-viscosity aqueous dispersion of negatively charged liposomes with liposome-entrapped EGF. The EGF/liposome composition is formed, in one embodiment of the invention, by suspending a lipid mixture typically containing equimolar amounts of neutral and negatively charged phopholipids and cholesterol in a low-conductivity aqueous medium containing EGF and a zwitterionic compound whose isoelectric point is between pH 5.5 and 8.5 to form a gel-like composition. One embodiment of the invention contains EGF entrapped by surface adsorption to the liposomes, for slow release from the composition.

30 Claims, 9 Drawing Sheets

EGF/LIPOSOME GEL COMPOSITION AND METHOD

FIELD OF THE INVENTION

The present invention relates to a high-visoisity EGF/liposome composition, and to methods of making and using the composition.

REFERENCES

Bronaugh, R. L., et al, J. Pharm. Sci., 72:64 (1985).

Buckley, A., et al, Epidermal Growth Factor increases Granulation Tissue Formation Dose Dependently. J. Surg. Res. 43, 322 (1987).

Buckley, A., Davidson, J. M., Kamerath, C. D., Wolt, T. B., and Woodward, S. C., Sustained Release of EGF Accelerates Wound Repair. Proc. Natl. Acad. Sci. USA 82, 7340, (1985).

Chowhan, Z. T., Yotsuyanagi, Y., and Higuchi, W. I., Biochem. Biophys. Acta 266:320–342, (1972).

Franklin, T. S., et al., Acceleration of Wound Healing by Recombinant Human Urogastrone. J. Lab. Clin. Med., 108,103, (1986).

King, L. E. and Carpenter, G. F. Epidermal Growth Factor. In: Goldsmith, L. A. (ed), Biochemistry and Physiology of the Skin. New York, Oxford University Press, 1983, pp. 26914 281.

Knauer, D. J. et al, Relationship between Epidermal Growth Factor Receptor Occupancy and Mitogenic Response. J. Biol. Chem. 259 (9), 5623–5631 (1984).

O'3 Keefe, E. et al, Invest. Dermatol. 78, 482 (1982).

MacDonald, R. C., and Simon, S. A., Proc. Natl. Acad. Sci. USA 84:4089–4093, (1987).

Mayhew, E., et al, Exp. Cell Res. 171:195 (1987).

Schwinke, D. L., Ganesan, M. G., and Weiner, N. D. J. Pharm. Sci. 72:244–248, (1983).

Szoka, F., et al, Proc. Nat. Acad. Sci, US, 75:4194 (1978).

Szoka, F., et al, Ann. Rev. Biophys. Bioeng., 9:467 (1980).

Tallarida, R. J., et al, in *Manual of Pharmacologic Calculations with Computer Programs*, Springer-Verlag, NY, pp. 72.

BACKGROUND OF THE INVENTION

Epidermal Growth Factor (EGF) is a widely distributed endogenous polypeptide (King). It is a powerful mitogen with high affinity receptors in both fibroblasts and epidermal keratinocytes, and has been shown to accelerate wound healing in vivo (O'Keef; Knauer). The first 5–10 days after injury are the most critical period during which maximal differences are seen between EGF treated and untreated wounds. EGF application after this period produces no significant improvement over controls, since by this time reepithelialization has already occurred in both groups. Due to its relatively short half life of about one hour, (Buckley, 1987), loss of occupied receptors through turnover and a lag time of 8–12 hours to commit cells to DNA synthesis (Knauer), it is necessary to apply EGF frequently to a wound to maintain effective local concentration during the critical period of initial wound healing (Buckley, 1987; Buckley, 1985; and Franklin, 1986). Thus, effective EGF therapy depends on frequent or sustained application of the drug during the first several days of wound healing.

For superficial wounds, local concentration of EGF can easily be maintained by frequent applications. For surgical incisions and full thickness skin wounds requiring suture repair, frequent application is not possible and a sustained-release formulation of EGF must be used for these uses. Implanted sponges have demonstrated the advantages of sustained EGF release in an animal wound model (Buckley, 1985) but would not be suitable as a dosage form.

SUMMARY OF THE INVENTION

It is therefore one object of the invention to provide a high-viscosity EGF/liposome composition which can be applied to a wound or surgical incision, for retention and sustained release of EGF at the site of application.

It is another object of the invention to provide a method for treating a wound or incision with such composition.

The EGF/liposome composition of the invention includes a high-viscosity suspension of negatively charged EGF/liposomes, i.e., liposomes containing EGF in liposome-entrapped form. The EGF/liposomes (i) contain neutral phospholipid, and at least about 10 weight percent negatively charged phospholipid, and preferably, between 20–50 weight percent each of neutral phospholipid, negatively charged phospholipid, and cholesterol. The total lipid concentration of the EGF-/liposomes in the composition is at least 50 mg/g composition and preferably between 50–200 mg/g composition. The EGF may be entrapped in the EGF-/liposomes by encapsulation or surface adsorption or a combination of both.

The high viscosity EGF/liposome composition may be prepared in a gel or paste-like state. The gel state is produced, according to another aspect of the invention, by mixing the above-noted vesicle-forming lipids with a low conductivity aqueous medium, preferably a low-conductivity (low ionic-strength) buffer which contains a zwitterionic compound whose isoelectric point is between about 5.5 and 8.5.

At a pH substantially above or below the isoelectric point of the zwitterionic compound, the medium contains charged electrolyte (the charged zwitterionic compound), and the composition exists in a non-gelled or only partially gelled state. In this state, the composition is easily processed, for example to absorb EGF, remove free EGF, and/or size and filter sterilize the composition. By adjusting the pH of the suspension to the isoelectric point of the zwitterionic compound, the aqueous medium becomes essentially non-ionic, and the composition assumes a gel state.

The composition is formed in a paste-like state by mixing a fluidic EGF/liposome composition with empty liposomes, to a final lipid concentration of at least about 300 mg/g composition and preferably between about 400–500 mg/g composition. The empty liposomes are preferably uncharged, and contain between about 20–50 mole percent cholesterol.

The EGF/liposome composition is used, according to another aspect of the invention, in a method for treating a surface wound or surgical incision, by sustained release of the composition from the wound or incision site.

These and other objects and features of the invention will become more fully apparent when the following detailed description of the invention is read in conjunction with the accompanying drawings.

DETAILED DESCRIPTION OF THE INVENTION

I. Viscous EGF/Liposome Compositions

Figure 1:
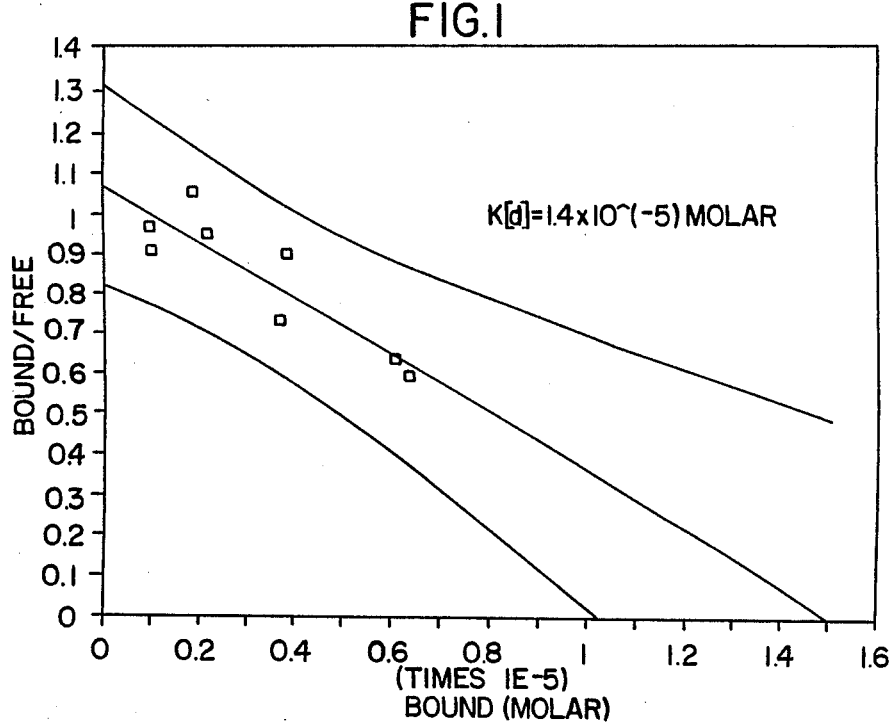
FIGS. 1 and 2 are Scatchard plots of EGF binding to EPG/EPC and EPG/EPC/cholesterol liposomes, respectively.

This section describes components and methods used in forming the high-viscosity EGF/liposome composition of the invention.

A. Definitions

As used herein, the terms below have the following meaning:

1. "Neutral phospholipid" refers to any vesicle-forming lipid having (i) two hydrocarbon-chain moieties which are effective to produce a stable bilayer formation, and (ii) a polar head group with no net charge at a pH between about 5.5–8.5.

2. "Negatively charged phospholipid" refers to any vesicle-forming lipid having (i) two hydrocarbon-chain moieties which are effective to produce a stable bilayer formation, and (ii) a polar head group with a net negative charge at a pH between about 5.5–8.5.

3. "Cholesterol" refers to cholesterol or any related sterol capable of combining with phospholipids to form stable lipid-bilayer vesicles.

4. "Epidermal Growth Factor" or "EGF" refers to human-EGF (h-EGF), typically recombinantly produced human EGF (rh-EGF), and to related peptides having the requisite ability to promote the growth of a variety of cells of epithelial origin in vitro.

5. "High-viscosity" refers to a gel-like or paste-like consistency which can be applied by squeezing from a tube or syringe, but which is sufficiently non-flowable, once applied, to be retained in bolus form at a wound or incision site for at least several hours.

6. A "low-conductivity aqueous medium" refers to an aqueous medium having an ionic strength which is less than that of a fully

B. Lipid Components

EGF/liposomes formed in accordance with the invention are prepared to contain between 10–90 weight percent neutral phospholipid, and 10–50 weight percent negatively charged phospholipid, and preferably between about 20–50 weight percent each of neutral phospholipid, negatively charged phospholipid, and cholesterol.

Neutral phospholipids having a variety of acyl chain groups of varying chain length and degree of saturation are available, or may be isolated or synthesized by well-known techniques. In general, partially unsaturated phosphatidylcholine (PC), such as egg PC (EPC) is readily obtained and provides suitable liposome characteristics, such as ease of extrusion and rate of release of liposome-entrapped EGF.

Likewise, negatively charged phospholipids having a variety of acyl chain groups of varying chain length and degree of saturation are available, or may be isolated or synthesized by well-known techniques. A variety of negatively charged phospholipids, such as phosphatidylglycerol (PG), phosphatidylserine (PS), and phosphatidylinositol (PI), can be used. One preferred phospholipid is partially unsaturated PG, such as egg PG (EPG). The negatively charged phospholipid in the composition serves two important roles. First, it imparts a negative charge to the lipid bilayer membranes, providing an electrostatic interaction between the membrane and the positively charged EGF The adsorption of EFG to the liposomal membrane will be discussed below. Secondly, the relatively high surface charge is important in the formation of a gel like liposome state which is characterized by a low lipid concentration and high viscosity.

Cholesterol is known to increase the stability of liposomes and, in the case where the phospholipid components are relatively unsaturated, to increase the packing density of the lipids in the liposomal bilayers. The effect of cholesterol on the rate of EFG release from EFG composition has been examined both in vitro and in vivo, as detailed below in Section II. Briefly, cholesterol significantly increased the half-life of EGF release in vivo.

One advantage of cholesterol in the EGF/liposome composition is potentially reduced toxicity due to lipid exchange between the liposomes and cells at the wound or surgical site. It has been demonstrated, for example, with several cultured tumor cell lines that EPG/EPC liposomes inhibit cellular growth in vitro, and that for at least some cell lines, this inhibition can be greatly reduced by the addition of cholesterol to EPG/EPC liposomes (Mayhew).

It is understood that the liposomes in the EGF-/liposome composition may contain a variety of other lipid components which may enhance liposome stability, viscosity, or EGF release characteristics, and/or materials cost. For example, the liposomes may include α-tocopherol, or pharmaceutically acceptable analogue thereof, at a total concentration of between about 0.1 to 2 weight percent, to improve lipid stability on storage.

C. Preparing an EGF/Liposome Gel Composition

The EGF/liposome gel composition of the invention can be prepared conveniently by a modified thin-film hydration method. In this method, vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder like form.

This film is covered with hydration medium and allowed to hydrate, typically over a 15-60 minute period with agitation. The size distribution of the resulting multi lamellar vesicles (MLVs) can be shifted toward smaller sizes by hydrating the lipids under more vigorous agitation conditions. The final concentration of EGF/liposomes is at least 50 mg/g and preferably between about 50-200 mg/g composition, and this can be achieved readily by hydrating a given quantity of lipid with approximately 5-20 volumes/weight hydration medium.

According to an important feature of the invention, it has been discovered that hydration of the vesicle-forming lipids with a low-conductivity aqueous medium containing a zwitterionic compound at the isoelectric point of the compound between pH 5.5 and 8.5, produces a liposome composition which is both gel-like in consistency and viscosity, and has a relatively low lipid concentration.

More specifically, the combination of net negative surface charge on the liposomes (due to the presence of at least about 10 weight percent negatively charged phospholipid) and the low-ionic strength of the aqueous medium and the unchanged zwitterionic compound produces a liposome composition characterized by (a) a viscous, gel-like consistency and (b) a relatively low lipid concentration, e.g., 50-200 mg/g composition.

Neutral amino acids, such as glycine, isoleucine alanine, proline, and valine are preferred zwitterionic compounds. The concentration of zwitterionic compound in the buffer is at least about 0.5 percent by weight and preferably between about 1-5 percent by weight, and the buffer is adjusted in pH to the isoelectric point of the compound to achieve the gel state.

The aqueous medium buffered with zwitterionic compound may initially be adjusted to a pH at which the zwitterionic compound is substantially in a charged form, so that the medium has a relatively high electrolyte concentration, i.e., a relatively high conductivity By adjusting the pH to the isoelectric point of the zwitterionic compound, typically after lipid hydration and liposome formation, the compound becomes non-electrolytic, i.e., has the desired low conductivity.

In forming the liposome gel composition directly, the low conductivity buffer is added to the lipid film, and the mixture is agitated until the desired liposome gel forms. The hydration step is generally effective to produce a homogeneous liposome suspension, where relatively small lipid quantities are involved For larger lipid amounts, the hydrated suspension may contain particles of non-hydrated or partially hydrated lipids This suspension can be converted to a homogeneous suspension by further processing, preferably by extrusion through a defined-pore size membrane, such as a 2 micron pore size polycarbonate membrane The extrusion step, of course, also reduces the size heterogeneity in the suspension. This general procedure for preparing a liposome gel suspension is illustrated in Example 1.

Alternatively, the liposome gel composition can be formed in two stages, involving initial liposome formation of a fluidic liposome suspension, by addition of the aqueous buffer in an electrolytic condition (e.g., where the zwitterionic compound is not at its isoelectric point, and subsequent pH adjustment of the aqueous medium to a non-electrolytic state (isoelectric point of the medium), to produce the desired gel formation. This approach allows the liposome suspension to be processed, after liposome formation for example, to size and sterilize the suspension, as discussed below, in a convenient, low viscosity form, then brought to a final gel state by pH adjustment.

The aqueous medium used in forming the composition may contain dissolved EGF, at a suitable concentration The suspension formed in this manner includes encapsulated, liposome-adsorbed, and free EGF. Free EGF can be removed, if desired, by conventional methods, such as molecular sieve filtration or the like.

Alternatively, free EGF may be added to preformed liposomes at a suitable concentration, producing a suspension with liposome-adsorbed and free EGF. According to one aspect of the invention, it has been found that the in vivo release kinetics of EGF from EGF-/liposomes containing absorbed EGF only is comparable for EGF/liposomes prepared to include both adsorbed and encapsulated EGF (Example 5).

It will be appreciated that a variety of liposome preparation methods, including reverse-phase evaporation and solvent-injection methods (Szoka, 1978, 1980), can be adapted for preparation of the above EGF/liposome gel composition, using a non-electrolyte aqueous buffer in the liposome formation step.

D. Preparing an EGF/Liposome Paste Composition

The EGF/liposome paste composition of the invention is prepared from a fluidic, i.e., non viscous, EGF-/liposome composition having a lipid composition detailed above and lipid concentration of at least 50 mg/g and preferably between about 50-200 mg/g. This composition is then mixed with empty, preferably neutral, liposomes to a final lipid concentration at which the composition has a desired paste like consistency, typically between 300 and 500 mg lipid/g suspension.

The initial fluid EGF/liposome suspension can be prepared by one of a variety of known liposomepreparation methods, as above. These methods include, but are not limited to, thin-film hydration, reverse-phase evaporation (Szoka), and solvent injection. As above, EGF may be incorporated into the liposomes on formation or by addition to EGF to already formed liposomes to produce an EGF liposome composition with absorbed EGF only.

The empty liposomes used in preparing the final high viscosity preparation are preferably uncharged or substantially uncharged liposomes. One preferred composition includes between about 50-70 mole percent neutral phospholipid, preferably EPC or partially hydrogenated EPC and 30-50 mole percent cholesterol.

The empty liposomes may be prepared prior to mixing with the EGF/liposomes (or negatively charged liposomes, if EGF is added subsequently to the combined liposome suspension), employing conventional liposome methods such as those discussed above. Alternatively, the relatively dilute EGF/liposome suspension may be employed as a hydration medium, for the formation of uncharged liposomes, also yielding a liposome suspension containing both EGF/liposomes and empty liposomes.

As an illustration of the latter method, a dilute EGF-/liposome suspension which has been treated to remove free EGF, and sized and sterilized as below, is added to a thin film of sterile dehydrated neutral lipids to a final lipid concentration of preferably between 300-500 mg/g. Lipid hydration may be carried out with vigorous agitation and/or at a temperature of at least about 37° C. to promote a uniform liposome suspension, preferably under sterile conditions. The resulting composition will include relatively small negatively charged EGF/liposomes, and relatively large neutral liposomes.

E. Liposome Processing

The above EGF/liposome compositions may be further processed to (a) achieve smaller and or more uniform liposome sizes, (b) remove free EGF and/or (c) sterile the EGF/liposome preparation. As indicated above, these processing steps are preferably carried out with the compositions in a non viscous state. This is accomplished, in the gel formulation, by employing an aqueous medium whose pH is adjusted to produce a substantial electrolyte concentration, as described above. In the EGF/liposome paste formulation, the processing steps are preferably carried out before addition of the empty liposomes.

Where it is desired to produce a sterile EGF/liposome composition, the liposomes are preferably sized down to 0.2 to 0.3μ, to allow sterilization by filtration through a convention depth filter. Several techniques are available for reducing liposomes to this size range, including sonication, homogenization and extrusion through a defined pore size membrane. Extrusion of liposome through a small pore polycarbonate membrane has been used successfully, as has extrusion through asymmetric ceramic membranes (co-owned U.S. Pat. No. 4,737,323). The liposomes may be extruded through successively smaller-pore membranes, to achieve a gradual reduction in liposome size.

Free EGF can be removed, if desired, by conventional centrifugation, ultrafiltration, or gel filtration (molecular sieve) methods. When the EGF liposomes are sized by extrusion, free EGF is preferably removed following the extrusion step.

The EGF liposomes are preferably sterilized, where required, by filtration through a conventional depth filter, typically having a 0.22 micron particle exclusion size. This method can be carried out on a practical, high through-put basis only if the liposomes have first been sized down to about 0.2-0.3 microns or less.

From the foregoing, several advantages of the method of preparation of the gel and paste like EGF/liposome compositions can be appreciated. The gel composition can be prepared at a low lipid composition and thus is relatively inexpensive to manufacture. The final viscosity of the composition can be controlled by small changes in final ionic strength, produced either by addition or removal of ionic components, or by relatively small pH changes in a medium containing a zwitterionic buffer.

The gel liposomes can easily be prepared and processed in a dilute form, for example to remove EGF, size and sterilize the liposomes, then brought to a final viscous state by pH adjustment.

The paste composition can likewise be prepared in an initial dilute form convenient for EGF removal, and if desired, for sizing and sterilization, then brought to a paste-like consistency by addition of empty liposomes Since the only step in the liposome processing which is difficult to carry out under sterile conditions is EGF removal, the empty liposomes can be added after sterilization of the EGF/liposomes, without additional sizing and sterilization requirements Finally, as discussed in Section II below, EGF is adsorbed readily to the negatively charged liposomes in the EGF/liposome composition, allowing the composition to be prepared simply by mixing free EGF with preformed liposomes.

II. Properties of the Composition

A. Viscosity of the Gel Composition

The EGF/liposome gel composition of the invention is characterized by a high-viscosity gel like consistency which is maintained at a low ionic strength, but which collapses as ionic strength is increased. This feature is illustrated in the study described in Example 2. Here liposomes containing equal-weight amounts of EPG, EPC, and cholesterol were prepared in a 2.3% w/v glycine buffer at isotonic pH (pH 6.0) buffer, as detailed in Example 1, except that EGF was not added. The mean viscosity for the samples was $13.3 \times 10^3$ Cps (centipoise) at 1.0 per second shear rate, characterized by a thick, relatively non-flowing gel consistency. With addition of NaCl to a concentration of only 0.05% w/v (at about 8.5 mM), the material lost its gel-like properties, being quite fluid, with a mean viscosity of only about $2.7 \times 10^3$ Cps at 1 per second. Further relatively small decreases in viscosity were seen with further addition of NaCl to a final concentration of 0.2% w/v.

B. EGF Binding to Negatively Charged Liposomes

According to one aspect of the invention, it has been found that EGF may be entrapped in negatively charged liposomes by surface adsorption, and that the binding affinity of EGF for the liposomes is effective to produce slow release of adsorbed peptide both in vitro and in vivo. In the binding study reported in Example 3, liposome gel compositions formed from either PC/PG (equal weight ratios) or PC/PG/cholesterol (equal weight ratios) were prepared as in Example 1. Increasing amounts of EGF (iodine radiolabeled) were added to aliquots of each of the two compositions, and the mixtures were allowed to equilibrate for one week at 4° C. The ratio of bound to free EGF was determined from total radiolabel measured before and after centrifugation, and these values were plotted as a function of amount bound, yielding the plots in FIGS. 1 and 2 for the EPC/EPG and EPC/EPG/cholesterol compositions, respectively. Affinity constants $K_d$ were determined from these plots as described in Example 3. As seen from the two figures, the $K_d$ values are in the range $1-2 \times 10^{-5}$ molar for both compositions.

Figure 2:
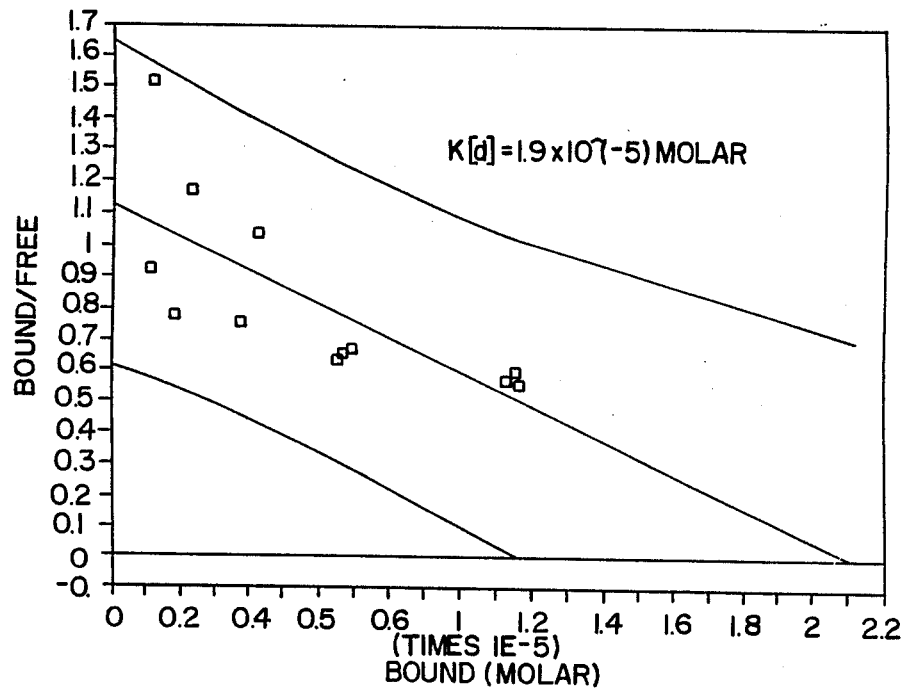

The number of EGF binding sites on the liposomes was determined from the x-axis intercept in the FIG. 1 and 2 plots, along with the calculated $K_d$ values, also as detailed in Example 3. From this, it was determined that at a peptide concentration of about 200 μg/ml, about 30% of the EGF is adsorbed at the lipid/water interface.

The adsorption of EGF to EPC/EPG and EPC/EPG/cholesterol monolayers was also examined in a lipid monolayer system, also as detailed in Example 3. Briefly, the method measures the ability of EGF to interpenetrate the lipid monolayer, as evidenced by changes in the interfacial surface pressure as EGF is added to the monolayer.

Figure 4:
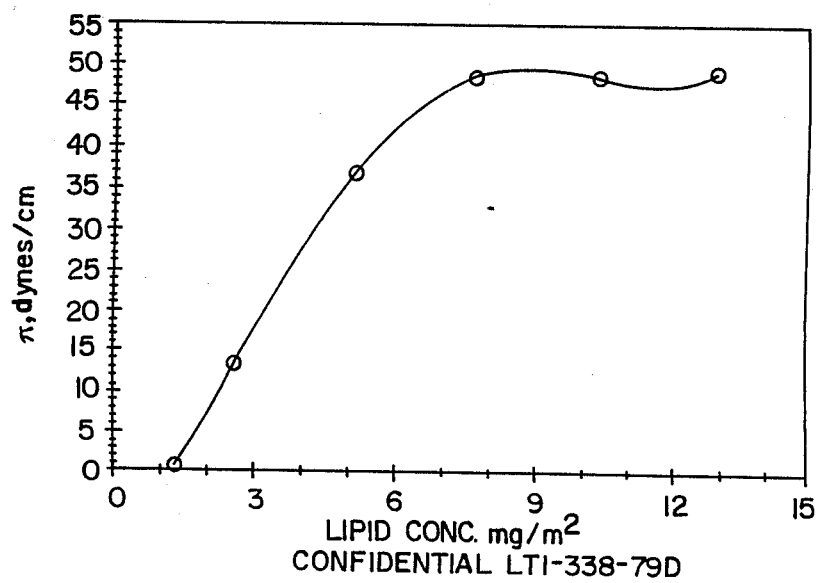
Figure 5:
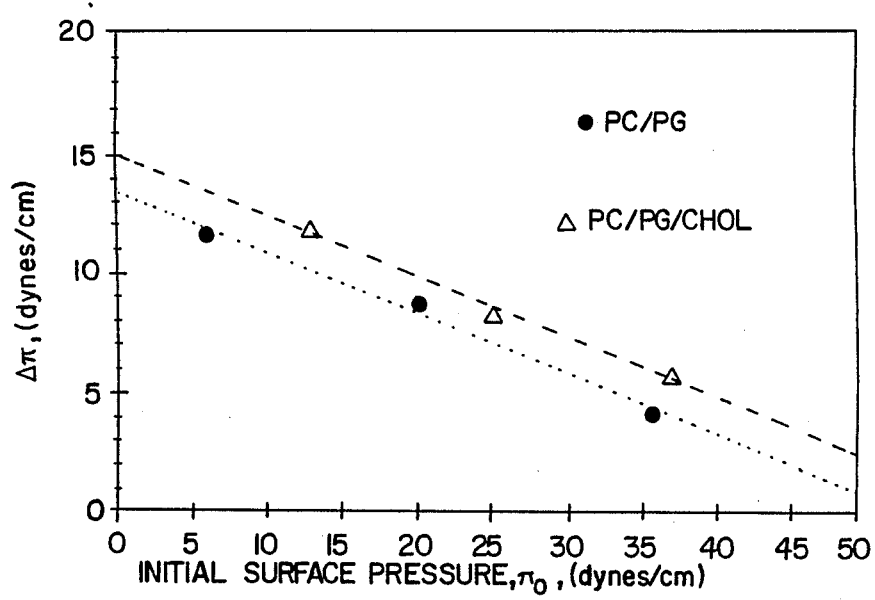
FIG. 5 is a plot of change in surface pressure, as a function of initial surface pressure, in the presence and absence of EGF in EPC/EPG/cholesterol liposomes (open triangles) and PC/PG liposomes (solid circles)

FIG. 4 is a plot of the interfacial surface pressure, $\pi$, as a function of lipid concentration for a EPC/EPG/cholesterol (equal wight ratios) lipid monolayers, as a function of lipid concentration. Similar plots were was made for EPC/EPG monolayers, and EPC/EPG/-cholesterol and EPC/EPG monolayers containing 40 μg/ml EPG, at each of several lipid concentrations. These plots were used to construct the graph of change in surface pressure due to the presence of 40 μg/ml EGF in the monolayer, as a function of surface pressure, for each of the two lipid compositions. This graph is shown in FIG. 5.

Using linear regression analysis to extrapolate to the y-axis intercept it can be seen that the change in interface surface pressure produced by EGF in the EPC/EPG/cholesterol composition is about 15 dynes/cm, and in the EPC/EPG composition, about 13.5 dynes/cm. The interface surface pressure attributable to EGF alone (no lipid interaction) is plotted in FIG. 3, and is μ.6 dynes/cm at 40 μg/ml. Thus for both lipid compositions, the measured change in surface pressure due to EGF in the presence of lipid is greater than that produced by EGF alone, indicating that the peptide is interacting with the monolayer.

The greater EGF-induced change in pressure seen in the EPC/EPG/cholesterol composition indicates a greater degree of EGF interaction with the addition of cholesterol to EPC/EPG.

C. In vitro EGF Release Characteristics

The kinetics of release of EGF from EGF/liposome compositions prepared according to the invention were examined in a standard two-chamber percutaneous absorption cell, as detailed in Example 4. The samples placed in the donor cell were suspended in 25% human serum in isotonic saline, for passage across a membrane filter into a donor collector compartment which was continually perfused with 25% human plasma in saline.

Figure 6:
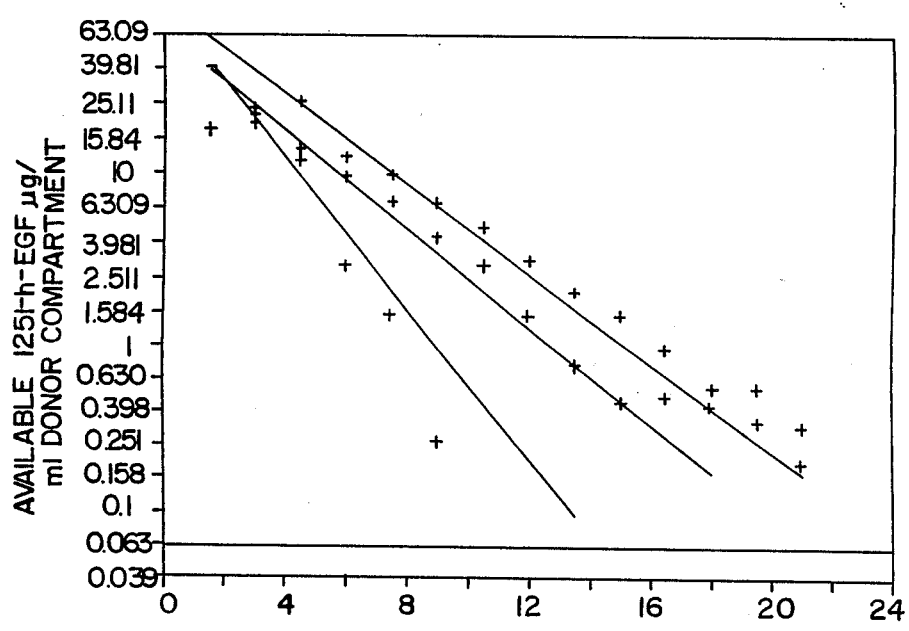
FIGS. 6-9 show the change in free EGF available in the donor compartment of a two compartment flux chamber, plotted as a function of time for free EGF (FIG. 6) and for three EGF/liposome compositions (FIGS. 7-9)

FIG. 6 shows release kinetics of EGF in the system for three independent kinetic Studies. The mean halflife of EGF release, calculated from the slope of the availability of free EGF in the donor compartment, as a function of time, is about 1.8 hours.

Figure 7:
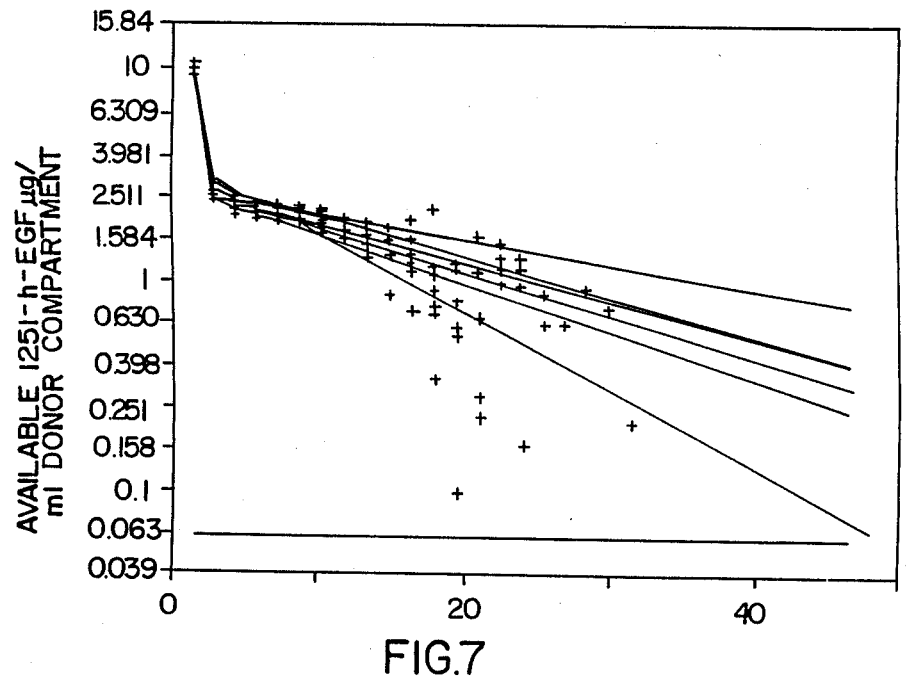
Figure 8:
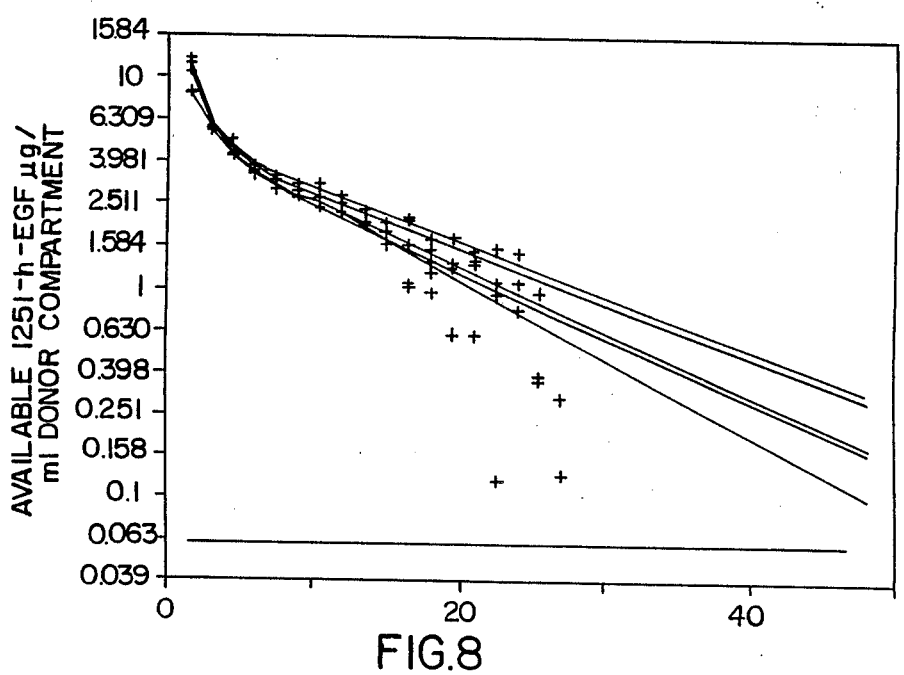
Figure 9:
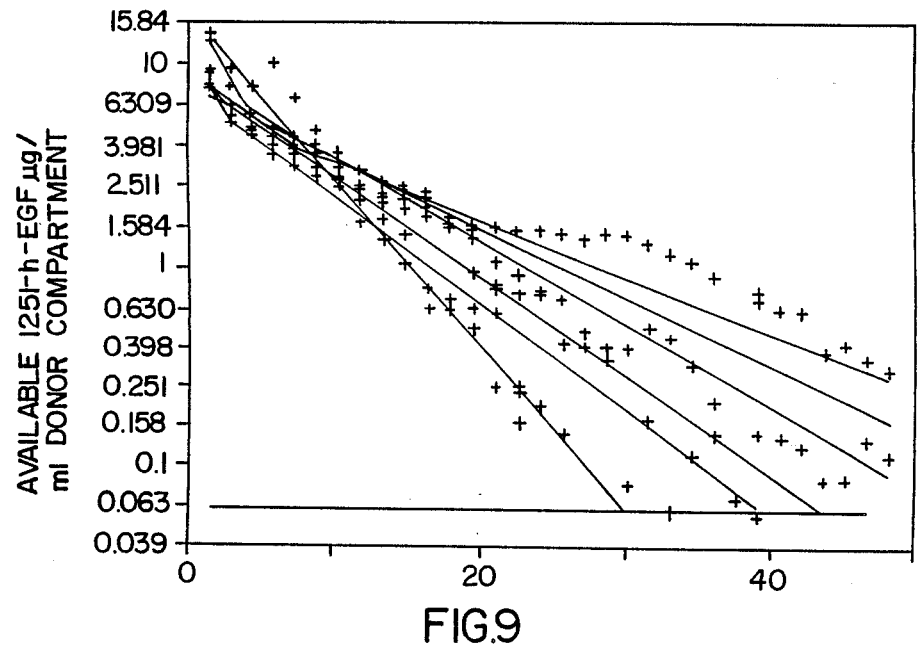
Figure 10:
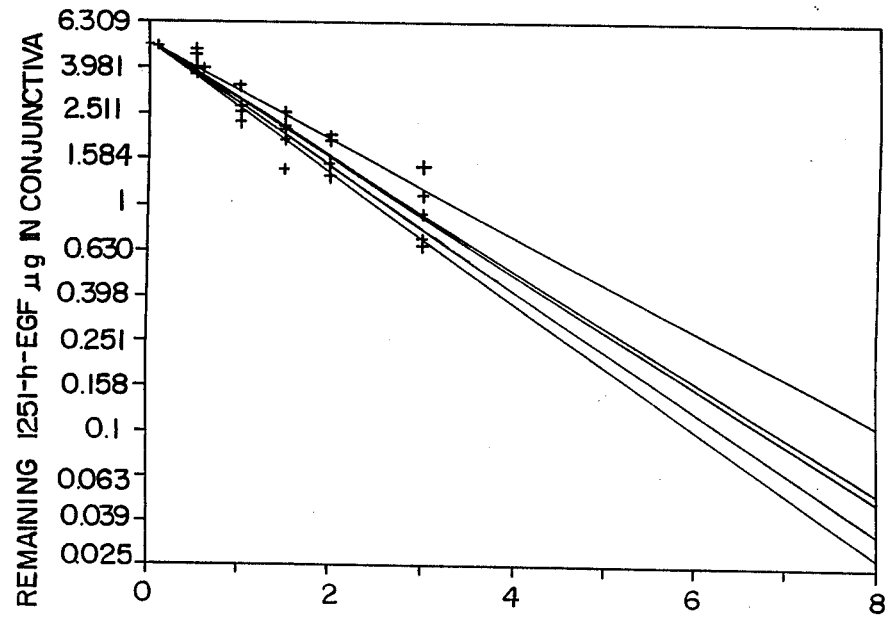
FIGS. 10-13 show the retention of radiolabled EGF, plotted as a function of time, for free EGF (FIG. 10), and for three EGF/liposome compositions (FIGS. 11-13)

The EGF available in the donor compartment from various EGF/liposome compositions were similarly measured. FIG. 7-9 shows plots of EGF available in the donor compartment, as a function of time, from (Composition I) EPC/EPG liposomes with encapsulated EGF (FIG. 7), (Compositions II) EPC/EPG/cholesterol liposomes with encapsulated EGF (FIG. 8), and (Composition III) EPC/EPG/cholesterol with adsorbed EGF. All three compositions contain free EGF, and thus also are expected to contain liposome-adsorbed EGF.

The model used to determine the half lives of EGF release from the liposomal formulations is discussed in Example 4. Briefly, the free EGF available in the donor compartment is determined from the measured rate of appearance of EGF in the receiver compartment, the rate constant $K_b$ of the membrane, and the volume $V_b$ of the external phase in the donor compartment. The calculated free available EGF in the donor compartment is then plotted as a function of time, as seen in FIGS. 7-14 9. The half lives of EGF release during the slow phases is determined from the resulting plots.

The half lives determined from above are 14.1 hours for the EPC/EPG composition (encapsulated EGF); 10.1 hours for the EPC/EPG/cholesterol composition (encapsulated EGF); and 6.2 hours for the EPC/EPG/-cholesterol composition (adsorbed EGF). It is clear that all of the liposome formulation enhanced the half life of EGF release in vitro severalfold over free EGF.

D. In vivo EGF Release Characteristics

According to an important feature of the invention, the high-viscosity EGF/liposome compositions of the invention are effective to (a) remain physically localized at a site of injection or administration and (b) provide a source of therapeutic levels of EGF over a several-day period.

Figure 11:
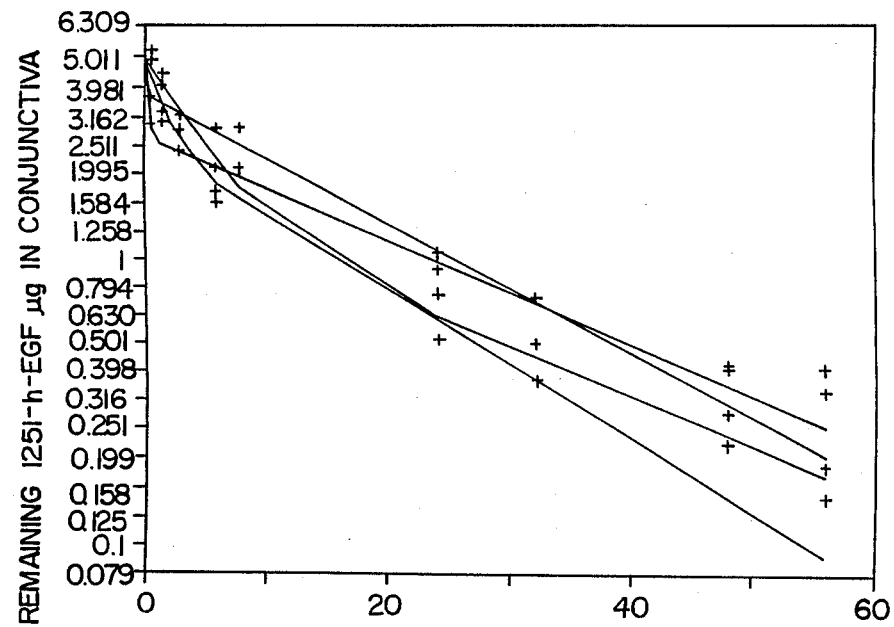
Figure 12:
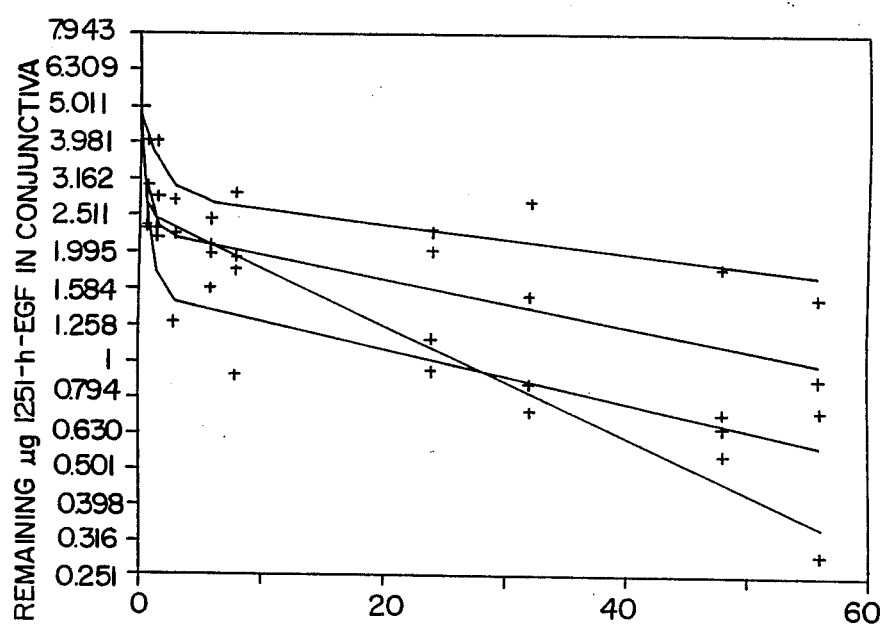
Figure 13:
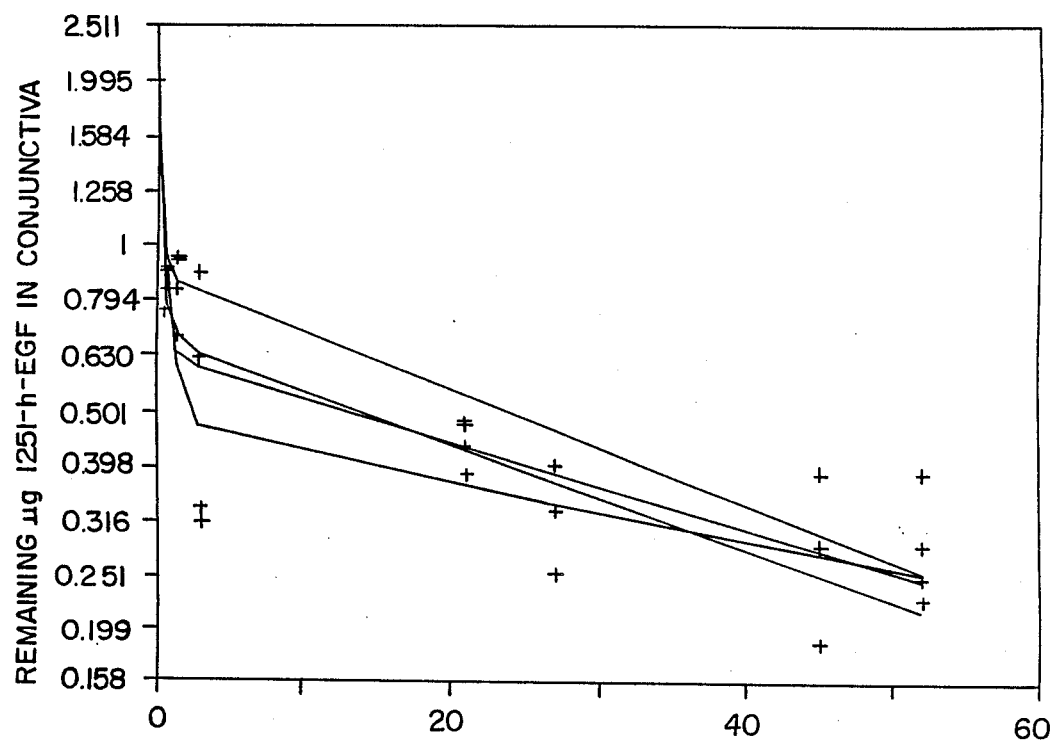

The enhanced retention of EGF in an EGF/liposome composition has been demonstrated with conjunctival placement of the various EGF compositions by subconjunctival-injection, and monitoring of levels of EGF retained at the conjunctival site over a several day period. The retention of radiolabeled EGF at a conjunctival site of administration, as a function of time after injection is shown in FIGS. 11-13 for free EGF (FIG. 10), and EGF/liposomes composed of: (Composition I) EPC/EPG and containing free and encapsulated EGF (FIG. 11), (Composition II) EPC/EGF/cholesterol and containing free and encapsulated EGF (FIG. 12), and (Composition III) EPC/EPG/cholesterol and containing free and adsorbed EGF only (FIG. 13). As seen, all of the EGF/liposome compositions give biphasic EGF release characteristics, indicating a burst of EGF released into the site of administration, followed by a slow phase EGF release over a several-day period.

Table 3 in Example 5 gives the half-lives of EGF release, and the percent EGF released in the burst for free EGF and the three EGF/liposome compositions, calculated from the mean values of the data plotted in FIGS. 10-13. The half life of EGF retention was extended from 1 hour for free EGF to 14-35 hours for the liposomal compositions. Interestingly, and in contrast to the in vitro release kinetics observed, the largest half lives (32 and 35.6 hours) were obtained with Composition II and III (cholesterol-containing EPC/EPG liposomes), whereas the shortest half life (14 hours) was obtained with the Composition I. This discrepancy with the in vitro kinetics data may be due to the greater stability of cholesterol-containing liposomes in vivo, perhaps related to the reduced extent of lipid exchange which would be expected between liposomes and cells at the site of administration in the presence of cholesterol.

The long-term availability of EGF in the region of the EGF/liposomes is seen from the data in Table 4 of Example 5. For free EGF, substantially no EGF was available at the conjunctival site one day after administration. With the EGF/liposome formulations, more than 1% of the total EGF was available at the site 4 days after administration for Composition I, six days after administration, for Composition III, and seven days after administration, for Composition II.

From the foregoing, it can be appreciated that the degree of retention of EGF/liposomes at a site of administration can be selectively varied according to the amount of cholesterol included in the liposomes, at least over the range from about 0-33 weight percent.

The above results also indicate that liposome-adsorbed EGF in the EGF/liposomes is released from the liposomes in vivo at substantially the same rate as encapsulated EGF. This result confirms that EGF is tightly bound to negatively charged liposomes (containing at least 20 mole percent negatively charged phospholipid), and that an effective EGF/liposome formulation can be made by surface adsorption to liposomes.

III. Utility

A. Topical Administration

The EGF/liposome composition is designed for application to burns and other skin wounds, to promote healing. The viscous material may be applied directly to the skin or in a skin dressing.

The material is preferably supplied in gel form from a tube or the like which can be easily applied to the skin or to a skin dressing. One unique property of the gel material, when applied directly to the skin as a film, is that salts in the skin will break down the gel structure, producing a fluid lipid dispersion as the material is rubbed in the skin.

B. Surgical Wound Administration

The viscous EGF/liposome composition is also useful for treating surgical incision, by application to the incision area before suturing. In this application, the high viscosity of the material reduces loss of material from the incision site, and the slow release of EGF from the liposomes provides a therapeutic level of EGF at the site over a several day healing period.

The gel or paste material is preferably applied directly to the incision area from a tube or syringe. In one embodiment, designed especially for long term storage, the liposome composition is reconstituted immediately before use, with addition of sterile water One of the problems which may be encountered when EGF/lipid material is reconstituted is incomplete mixing and lipid hydration, due to the viscous consistency of the material as it rehydrates. The problem of incomplete or nonuniform hydration can be overcome, in forming the EGF/liposome gel composition of the invention, by suitable adjustments in pH during the gel-forming process, to allow initial lipid hydration in a relatively fluidic form, with gradual transformation to a gel form. The required change in pH may be produced by addition of an acid or base following lipid hydration, or may result from the release of an acid or base species from a reservoir present in the dehydrated lipid mixture.

As an example, the dehydrated lipid mixture may be prepared from EGF liposomes having an encapsulated zwitterionic compound, where the zwitterionic compound is in a predominantly charged form and the initial suspension is largely freed of extraliposomal (nonencapsulated) compound prior to dehydration. The rehydration medium, in turn, may be an unbuffered medium whose initial pH is different from the isoelectric pH of the encapsulated compound, but which after complete equilibration with the encapsulated compound occurs, yields the desired isoelectric pH.

Following rehydration and reformation of liposomes, slow release of the charged zwitterionic compound from the liposomes would produce a gradual pH shift toward the desired pH at which the compound is largely non-ionic, producing increasing suspension viscosity. After final set up, the material is forced from the tube or syringe in gel form into the incision site.

C. Ophthalmic Uses

Figure 14A:
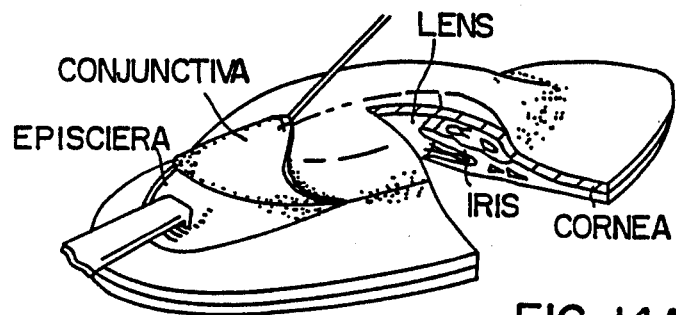
FIG. 14A-14C illustrate surgical steps in a corneal implant operation.
Figure 14B:
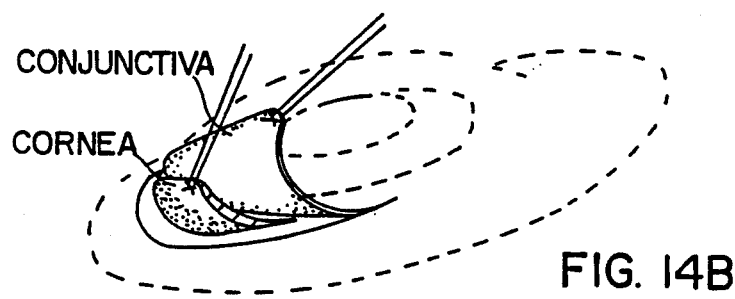
Figure 14C:
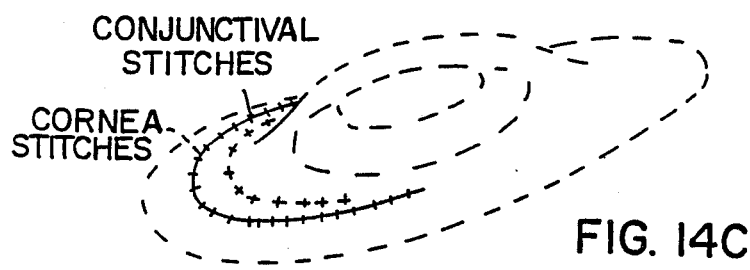

FIGS. 14A-14C illustrate surgical incision and incision repair step in a corneal replacement or transplant operation. An initial arcuate incision in the conjunctiva, illustrated in FIG. 14A, allows the conjunctiva to be pulled away, exposing the underlying episclera and cornea. A second arcuate cut in the cornea, shown in FIG. 14B, allows the cornea to be pulled back to provide access to the lens (not shown) After surgical removal or replacement of the lens, the cornea is first closed by stitching, seen at 20 in FIG. 15C, followed by closure of the conjunctiva by stitching, indicated at 20. Post-operative healing involves healing of the two incisions, and regrowth of the episclera layer between the conjunctiva and cornea.

Figure 15A:
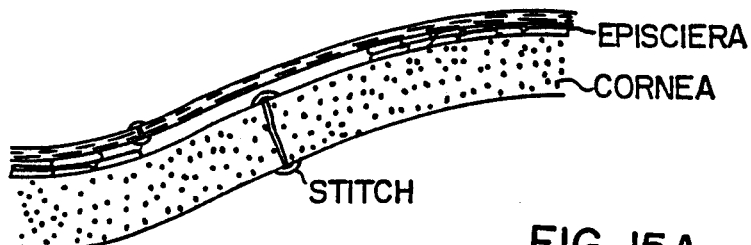
FIGS. 15A-15C are diagrammatic cross sections of the surgical region of an eye seen in FIGS. 14A-14C, showing in FIG. 15B the introduction of an EGF-/liposome formulation prepared according to the invention, and in FIG. 15C, the residual composition in the eye after an extended release period.
Figure 15B:
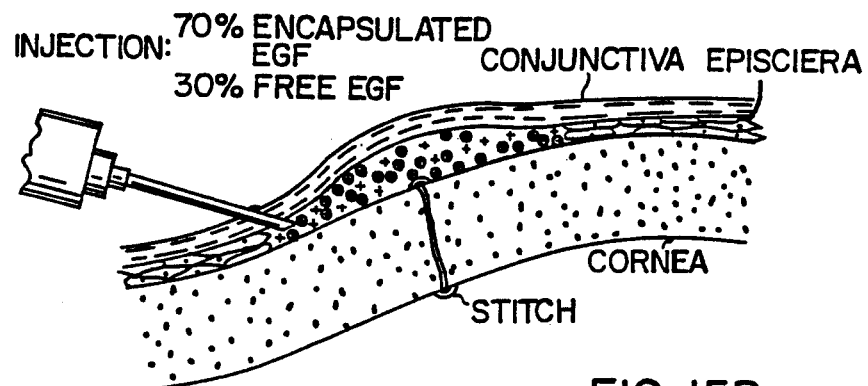
Figure 15C:
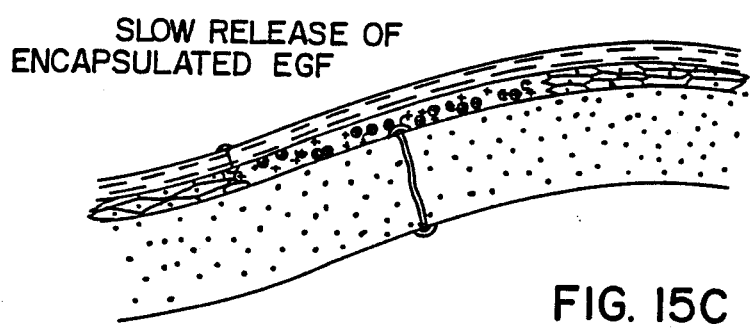

FIGS. 15A-15C illustrate the use of the EGF/liposome composition of the invention to promote healing of the above described ophthalmic surgery. FIG. 15A shows a cross section through an outer portion of the stitched cornea and conjunctiva, as seen in perspective in FIG. 14C. After stitching, the space between the conjunctiva and cornea is filled with an EGF/liposome composition, by inserting a needle through a region of the stitched incision in and injecting the composition into the episclera space. As illustrated in FIG. 15B, the material may be injected until a slight bulging of the conjunctiva is produced.

The injected material remains in place, over a several day period, by virtue of its gel or paste-like consistency. EGF is released into the surrounding area, promoting healing of both stitched incisions and regrowth of the episclera over an extended healing period.

Preliminary studies conducted in support of the present invention have examined the effect of viscous EGF/liposomes on ophthalmic inciSion repair in an animal model system. Briefly, it has been found that a viscous EGF/liposome composition provides greater wound repair, as measured by the strength of the repaired incision several days after treatment, than empty liposomes The following examples are intended to illustrate various compositions, methods of preparations, and characteristics of the present invention The examples are in no way intended to limit the scope of the invention.

Example 1

Preparation of EGF/Liposome Compositions

EPG was purchased from Avanti Polar Lipids (Birmingham, Ala.) and EPC was purchased from Asahi Chemical Company (Tokyo, Japan). Cholesterol was from Croda, Inc. (New York, N.Y.) and $\alpha$-tocopherol (Vitamin E) from Hoffman - La Roche (Nutley, N.J.). Aminoacetic acid (glycine) was from J. T. Baker (Philipsburg, N.J.).

EGF from yeast (Chiron) was a gift of Ethicon, Inc. (Somerville, N.J.). $^{125}$I-labeled rh-EGF (3-[$^{125}$I] iodotyrosyl human recombinant epidermal growth factor was purchased from Amershal Corporation (Arlington Heights, Ill.). $^{125}$I rh-EGF was shipped the day of iodination and used only for the first four weeks following iodintion.

Liposomes were prepared by thin film hydration of a dehydrated lipid mixture containing one of the following lipid mixtures. Composition I: EPG/EPC/$\alpha$-tocopherol (1/1/0.03, w/w/w) and Composition II: EPG/EPC/cholesterol/ -tocopherol (1/1/1/0.03, w/w/w/w). The lipids were dissolved in chloroform:methanol (2:1) and a total of 33 g of lipid were added to a round bottom flask and dried in vacuo to a thin film. To this film was added 267 ml of hydration buffer containing 2.3% (w/v) glycine, pH 6.0. Hydration was carried out for 1-2 hours with swirling. The material had a stiff, gel like consistency.

The materials were prepared in a biological cabinet using sterilized equipment, filter-sterilized lipid, and filter sterilized aqueous solutions to keep the bioburden as low as possible. The vesicles were prepared by thin-film hydration in a 2.3% glycine buffer. The resulting liposome dispersion was injected by extrusion through a Gelman Acrodisc into 1 or 10 ml plastipak syringes which were wrapped in aluminum foil and labeled. An aliquot of the liposome gel was set aside, and "collapsed" back into a lotion by the addition of concentrated saline.

Samples were assayed for rh-EGF concentration, total lipid phosphate, cholesterol content, pH, viscosity, osmolarity, particle size and pyrogen levels (Table 1). Mean diameters were assayed using the Nicomp laser particle sizer.

TABLE 1

Characterization of EGF Compositions

| Assay (units) | rh-EGF-Loaded "Lotion" | rh-EGF-Loaded "Gel" | Placebo "Lotion" | Placebo "Gel" |
|---|---|---|---|---|
| rh-EGF ($\mu$g/gm) | 192 | 197 | 0 | 0 |
| Total Lipid Phosphate ($\mu$mol/gm) | 91.1 | 100.4 | 87.0 | 87.0 |
| Cholesterol (mg/gm) | 31.6 | 31.6 | 34.3 | 32.2 |
| Buffer pH | 6.1 | 6.1 | 6.0 | 6.0 |
| Osmolarity (mOsm) | 326 | 313 | 319 | 305 |
| Viscosity (Cps) [c] | 2,750 | 17,700 | 3,600 | 20,500 |
| Nicomp Mean Diameter (nm) | 630 | 713 | 644 | 666 |
| LAL Pyrogen Test | Pass | Pass | Pass | Pass |

Example 2

Viscosity of the EGF/Liposome Composition

Five separate batches composed of EPG/EPC/cholesterol/alpha-tocopherol (1/1/1/0.03, w/w/w/w) liposomes were prepared as described in Example 1. The viscosity of each of the batches was determined (a) without addition of NaCl, and after addition of (b) 0.05%, (c) 0.1, and (d) 0.2% by weight NaCl. At each salt concentration, the mean viscosity of the compositions tested was determined. The measured values, expressed as extrapolated Cps at 1 per second shear rate, are shown in Table I below.

Viscosity was determined using a Brookfield DV-II cone/plate viscometer. Viscosity readings were made at all relevant spindle speeds. Spindle speeds were converted to the shear rate. Plots of log (viscosity) versus log (shear rate) were prepared from which the viscosity at a shear rate of one reciprocal second was extrapolated.

TABLE 2

| % NaCl | Mean Viscosity (Extrapolated Cps at 1 sec. shear rate) |
|---|---|
| 0.0% | $13.3 \times 10^3$ |
| 0.05% | $2.7 \times 10^3$ |
| 0.1% | $1.5 \times 10^3$ |
| 0.2% | $0.8 \times 10^3$ |

The mean viscosity of the composition in the absence of NaCl corresponds to a stiff, gel-like consistency. As seen, addition of only a slight amount of salt reduces the viscosity severalfold, producing a thinner, lotion-like consistency.

Example 3

Adsorption of EGF to Liposomes

A. Scatchard Analysis

The affinity of EGF binding to liposomes and the number of binding sites in the Example 1 liposomes can be determined from Scatchard analysis of the binding of radiolabled rh-EGF to the liposomes.

Liposomes formulations I and II in Example 1 were prepared by hydration of the thin lipid film with 2.3% glycine (w/w), as described in Example 1. The formulations were sized (three passes for each pore size) sequentially through 5.0 $\mu$m and then 1.2 $\mu$m polycarbonate filters, then extruded through a 0.4 $\mu$m Nuclepore filter.

Five $\mu$Ci of $^{125}$I-rh-EGF were added to 2 ml of rh-EGF, 1 mg/ml concentration in glycine buffer. Aliquots of this iodinated stock solution were added to duplicate, 1 ml samples of the liposome preparation also containing five final rh-EGF concentrations ranging from 6 to 100 $\mu$g rh-EGF per ml liposomes. The resulting preparations were allowed to come to equilibrium by incubation for one week at 4° C.

After equilibration, known volumes of the preparations were removed for gamma counting. A known volume of the bulk of the remainder of each sample was centrifuged for two hours at 40K RPM and 4° C. Known volumes of the clear supernatant ("free" EGF) were removed for gamma counting. Any remaining supernatant was removed and discarded. Each liposome pellet was resuspended in 1.2 ml of 1% (w/w) Triton X-100 and vortexed. All samples were then assayed for gamma counts, and the actual CPM per ml were determined.

The ratio of bound/free was determined for each sample as:

Ratio=[bound]/([bound plus free]−[bound])   (Eqn. 2)

Values of [bound]/[free] versus [bound] were plotted and the data fit to a linear least squares regression. FIGS. 1 and 2 show the plots for the I and II formulations, respectively. $K_d$, the binding constant of the peptide on the liposomes was determined from the slope of the regression line, which was taken to be $1/K_d$. Confidence intervals of $K_d$ were calculated according to known methods (Tallarida).

The results seen in FIGS. 1 and 2 indicate that there is no significant difference between the two formulations as to affinity constants, which is calculated as about $1-2 \times 10^{-5}$M for both formulations. The $K_d$ for liposomes is several orders of magnitude less than that for cultured fibroblasts ($2-4 \times 10-10$M) (Buckley, 1987).

The number of binding sites was determined from the X-axis intercept of the of the regression line, which was taken to be equal to [binding sites]$K_d$ (Scratchard). The EPC/EPG formulation had 0.8 $\mu$g EFG binding sites per mg lipid, and the EPC/EPG/cholesterol formulation had 1.4 $\mu$g EGF binding sites per mg lipid. The number of binding sites is actually the number of binding sites on the external face of the lipid bilayer. Thus, for large unilamellar vesicles, the actual number of binding sites would be twofold greater than for multilamellar or oligolamellar preparations like these, at least threefold greater. The lipid concentration used is sufficient to potentially adsorb all the rh-EGF.

Knowing the estimates for $K_d$ and the number of binding sites, it can be calculated that at this lipid concentration and at a peptide concentration of about 200 ug rh-EGF/gm formulation, about 30% of total rh-EGF is adsorbed at the lipid/water interface.

B. Surface Pressure Measurements

Adsorption of native rh-EGF lipid monolayers to lipid/water interfaces can be evaluated by measuring surface tension of lipid monolayers spread on an rh-EGF-containing aqueous subphase The methodology of Weiner and coworkers (Schwinke) was used to rank order different lipid monolayer compositions with respect to the enhanced ability of a peptide to interpenetrate a given monolayer. Distilled water adjusted to pH 6.0 was used as the subphase in these pilot experiments. Other experiments done in 2.3% glycine as buffer gave the same results.

Surface tension measurements were made on a CSC Scientific Model 70545 DuNouy tensiometer (Fairfax, Va.). Briefly, a new lipid monolayer was spread from a hexane/ethanol (95/5, v/v) solution for each determination. Surface pressure ($\pi$) was determined as the difference of the surface tension of test monolayer of subphase minus the surface tension of subphase alone. Delta $\pi$ is the difference between mean monolayer surface pressure in the presence and absence of rh-EGF. All data points are the mean of at least duplicate determinations.

Figure 3:
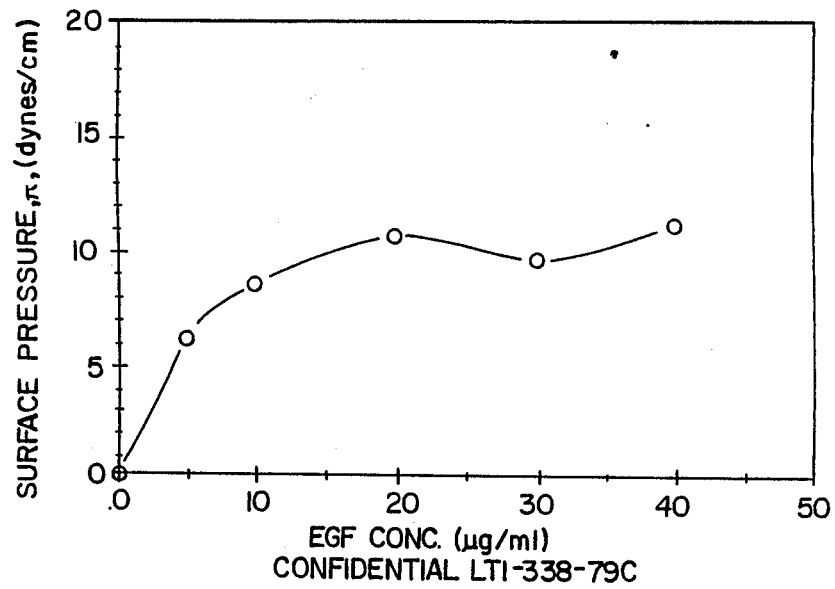
FIGS. 3 and 4 are plots of surface pressure, at an air/water interface, of aqueous EGF (FIG. 3) and EPG/EPC/cholesterol (FIG. 4), respectively, as a function of EGF and liposome concentration.

FIG. 3 is a plot of surface pressure $\pi$ of aqueous EGF measured as a function of EGF concentration. As illustrated in the figure, rh-EGF is a surface active peptide having a limiting pressure of 12.6 dyness/cm as determined from a double reciprocal transformation of this graph. Surface pressure changes also be monitored as a function of lipid concentration. As an example, EPG-/EPC/Chol (1/1/1, w/w/w) monolayers displayed a limiting pressure of 50.9 dyness/cm in the absence of rh-EGF in the aqueous subphase (FIG. 4). This limiting pressure (also called the collapse pressure) is considered to be the equilibrium pressure of liposome bilayers (MacDonald).

The ability of the peptide to interpenetrate the lipid layer can be determined, as indicated above, by measuring interfacial surface pressure in the presence and absence of peptide at several lipid concentrations. The difference in surface pressures (delta $\pi$) is plotted versus the surface pressure in the absence of peptide. In FIG. 16, data for EPG/EPC (1/1, w/w) and EPG-/EPC/Chol/a-toc (1/1/1, w/w/w/) are plotted. The rh-EGF concentration in the subphase was 40ug/ml. A linear regression analysis was carried out on the data to extrapolate to the y axis intercept (limiting $\pi$) (Wiener). The fact that this value, e.g., 15 dynes/cm for the EPC-/EPG/cholesterol formulation, is greater than the peptide's own limiting pressure in the absence of lipid monolayer, is evidence that the peptide is penetrating the lipid monolayer. That is, the observed effect is not merely competition for the surface by two different surface-active molecules (Schwinke). Furthermore, the formulations may be rank ordered according to the magnitude of the extrapolated peptide/lipid limiting $\pi$.

Based on this analysis, both Composition I (solid circles in FIG. 5) and Composition II (open triangles in FIG. 5) show rh-EGF adsorption to the lipid. The greater extrapolated value of delta $\pi$ for the EPC-/EPG/cholesterol formulation suggests that this composition formulation shows a greater degree of peptide/bilayer interaction than the EPG/EPC (1/1, w/w) formulation.

EXAMPLE 4

In vitro EGF Release Kinetics from EGF-/Liposomes

Liposome formulations were evaluated in vitro by release rates of 125 I-rh-EGF into the receiver compartments of percutaneous absorption cells that were continuously perfused with 25% pooled human plasma/saline.

A conventional two-chamber absorption cell, using a bath temperature of 37° C., was employed (Bronaugh). A 25 mm, 0.08 $\mu$m diameter Nuclepore (Pleasanton, Calif.) polycarbonate filter was used to separate the donor from the flow-through acceptor compartment. This pore size gave the shortest half life of free EGF passage—about 1.8 hours—without detectable passage of intact liposomes through the membrane. The $^{125}$I-rh-EGF preparation was mixed with an equal quantity of 25% pooled human plasma/isotonic saline and 200 $\mu$l aliquots were immediately applied to the donor compartments. Parafilm was used to occlude the donor compartment and prevent evaporative loss. The perfusate was collected by fraction collector into scintillation vials and mounted in a Packard TriCarg 20000. rh-EGF flux was calculated from the specific activity (DPM per $\mu$g peptide). Clearance rate half-lives were determined for individual percutaneous absorption cells as described below.

FIG. 6 shows the available radiolabeled rh-EGF in the donor compartment of three Bronough cells, as a function of time, for an rh-EGF solution. In this single phase system, it is possible to determine the concentration of peptide remaining in the donor compartment by subtracting cumulative peptide in the measured in the receiver compartment from total peptide applied to the donor compartment. The half-life of EGF release determined from the mean of the three EGF curves, is about 1.8 hours. Since the membrane is rate-limiting for EGF transfer from the donor to receiver compartment, the curve can also be used to calculate $K_b$, the rate constant of the membrane.

The determination of drug-release halflife from the pool of free EGF available in the donor compartment is more complicated, due to the fact that in EGF-/liposomes, only EGF which is located in the external aqueous phase is potentially bioavailable. A model proposed by Chowhan et al for solute flux from a liposomal carrier is represented by the following equation:

$$C_{II} = (dAs/dt) / (K_b * V_b) \qquad \text{(Eqn. 1)}$$

where, $C_{II}$ is the concentration of the solute of interest in the external aqueous phase, dAs/dt is the rate of solute appearance in the receiver compartment during the time period of interest, $K_b$ is the rate constant of the membrane separating donor and receiver compartments, and $V_b$ is the volume of the external phase in the donor compartment. The rate of solute appearance in the donor compartment was determined, as above, by assaying the amount of radiolabel in the donor compartment over the efflux period. $K_b$ was determined from the free drug efflux study above, and $V_b$ can be estimated to within about 10%. Using the equation above, the $C_{II}$, the available free EGF in the donor compartment, was calculated as a function of time. FIG. 7 shows plots for seven Bronaugh cells, where the heavier line represents the overlap of two or more plots.

The release profile of all liposome formulations was best modeled by bi-exponential fit. The slow-phase $t_{1/2}$ of Composition I EPG/EPC/a-toc (1/1/0.03, w/w/w) MLVs (FIG. 11) with free and entrapped rh-EGF was about 14.1 hours. "Free" rh-EGF in the external phase of the donor compartment was maintained above a concentration of 0.063 μg EGF/ml (the lower threshold of therapeutic activity) for over 50 hours.

FIG. 12 shows similar plots from five Bronaugh cells of the availability of free EGF in the donor cell, as a function of time, for an EGF/liposome composition having the Composition II formulation EPG/EPC/Chol/a-toc (1/1/1/0.03, w/w/w/w). As with the composition above, the liposomes contained liposome-encapsulated EGF, as well as liposome-adsorbed and free EGF.

The available, i.e., free EGF, in the donor compartment was determined as above. From the plots, a mean halflife of about 10.1 hours for the slow phase of the release kinetics was observed. Thus, free rh-EGF displayed a somewhat shorter $t_{\frac{1}{2}}$ than for the liposome formulation lacking cholesterol, although the two halflives are not statistically different.

In another study, rh-EGF was added to pre-formed EPG/EPC/Chol/a-toc (1/1/1/0.03, w/w/w/w) MLVs to give an initial external phase peptide concentration in the vicinity of 100 ug/gm formulation. The slow phase $t_{\frac{1}{2}}$ of this formulation (Composition III) was significantly longer (6.2 hrs, FIG. 13) than that of the free rh-EGF solution tested in the same model, and somewhat less than the above liposome compositions containing both encapsulated and liposome-entrapped EGF. The data indicate that release of adsorbed EGF from liposomes is rate limiting and occurs with roughly the same release kinetics as EGF which is both encapsulated in and adsorbed to the liposomes.

EXAMPLE 5

In vivo EGF Release Kinetics from EGF/Liposomes

Details of the EGF/liposome compositions tested are given in Table 1. All liposome formulations consisted of unsized multilamellar vesicles containing egg phosphatidyl glycerol and partially hydrogenated egg phosphatidyl choline, prepared substantially as in Example 1. All formulations contained glycine buffer (2.3%) as a gelling agent and a-tocopherol (0.1%) as an antioxidant. All formulations contained $^{125}$I-h=EGF (0.01 uCi/ug) as a radiolabel, and some contained a small amount of tritiated cholesterol (<0.1% of total lipid) as a formulation marker. Free EGF and Composition I contained Thimerosal (0.1%) and dimethylene-triaminetetraacetic acid (DTPA) (0.1%), but Compositions II and III did not. In addition Compositions II and III were prepared aseptically in an attempt to minimize irritation following administration.

Compositions II and III had the same lipid composition but were loaded differently. EGF was encapsulated into Composition II liposomes during formation, and therefore contained entrapped drug. EGF was added to the liposomes of Composition III after formation, and was therefore considered adsorbed to the liposome surface. Total EGF was adjusted to give similar quantities of EGF in the external aqueous phase in both compositions II and III.

TABLE 3

CHARACTERISTICS OF EGF FORMULATIONS

| | FORMULATION | | | |
|---|---|---|---|---|
| Type | Free EGF | Liposome I | Liposome II | Liposome III |
| | Free | Adsorbed and Entrapped | Adsorbed and Entrapped | Adsorbed |
| EPC, mg/g | 0 | 130 | 35 | 35 |
| EPG, mg/g | 0 | 130 | 35 | 35 |
| Cholesterol mg/g | 0 | 0 | 35 | 35 |
| EGF, ug/g | 100 | 100 | 100 | 40 |
| DTPA + Thimerosal | Yes | Yes | No | No |
| Aseptic Process | No | No | Yes | Yes |
| pH | 7.0 | 6.05 | 6.02 | 6.02 |
| EGF Dose, ug/kg body wt. | 2.3 | 2.1 | 1.6 | 0.63 |

Formulations of free or liposome associated $^{125}$I EGF were administered by subconjunctival injection to female New Zealand White Rabbits (2-3 kg). Conscious rabbits were placed in a bag restrainer, and 1-2 drops of Ophtaine 0.5% Ophthalmic Solution were administered to the eye as a local anesthetic 1 minute prior to the injection. A small fold of conjunctiva superior to the cornea was raised with forceps and 50 ul of the formulation injected slowly through a 27 ga needle using a calibrated glass microsyringe (Hamilton Co., Reno, Nev.). Both left and right eyes were used on separate days in some rabbits but no eye was used more than once during the study. Eyes were monitored for signs of leakage, inflammation or irritation. Small blebs formed following injection which tended to migrate slowly downward over a period of days. A liposome encapsulated dye appeared to remain localized in the eye for over 5 days following injection in one rabbit, thus indicating the ability of a formulation to remain physically localized at the injection site during the study.

The amount of radioactivity remaining in the injected eye was measured for up to 96 hours after injection (until at least 90% of the initial radioactivity had disappeared). An external NaI crystal detector/ratemeter (The Nucleus Model L) was placed directly over the eye and radioactivity measured for 2 minutes and recorded on a chart recorder. A standard curve was prepared by serial dilutions of the dose solution to calibrate and demonstrate the linearity of the detector response. The mean chart deflection during each recording was taken as the measurement at that time point. The first reading was taken immediately after injection ("zero time") and subsequent measurements were converted to a percentage of this initial amount.

Individual radioactivity versus time data were recorded for each animal, and the mean values for each animal group (N=4-6) were calculated. These data are plotted in FIGS. 10-13 which show the remaining $^{125}$I-rh-EGF in conjunctiva as a function of time following subconjunctival injection of (a) free EGF (FIG. 10), (b) Composition I EGF/liposomes (FIG. 11), (c) Composition II EGF/liposomes (FIG. 12), and (c) Composition III EGF/liposomes (FIG. 13). As seen from FIG. 11, unencapsulated EGF disappeared rapidly from rabbit eyes after subconjunctival injection (FIG. 1). This disappearance was first-order and had a half life of 1.0 hours. Less than 15% of the dose remained in the eye after 3 hours, with only $1 \times 10^{-31}$ 5% expected to remain after 24 hours. In contrast, EGF administered in liposome formulations disappeared much more slowly from the eye. Formulation I (EPC/EPG) exhibited a small initial burst disappearance followed by first-order disappearance with a half-life of 14.1 hrs (FIG. 11). Formulations II and III (EPC/EPG/CH) both exhibited a larger initial burst followed by a slower first order disappearance (Formulation II half-life: 32 hrs, Formulation III half-life 35.6 hrs).

Each plot was used to calculate first order rate constants for EGF disappearance from the eye for each formulation by a non linear least squares fitting method (RSTRIP, MicroMath, Salt Lake City, Utah). Where a significant initial burst release was observed, only the log-linear portion of the curve after the rapid initial phase was fitted. The calculated rate constants, half-life, and % of dose in the burst release are given in Table 2 below.

TABLE 4

IN VIVO PERFORMANCE OF LIPOSOME EGF FORMULATIONS

|  | Free EGF | FORMULATION | | |
|---|---|---|---|---|
|  |  | I (No cholesterol) | II (entrapped) | III (adsorbed) |
| Rate constant hr$^{-1}$ (a) | 0.69 | 0.049 | 0.022 | 0.019 |
| Half-life, hrs | 1.0 | 14.1 | 32.0 | 35.6 |
| Burst Release % of Dose | N/A | 15.0 | 43.0 | 57.0 |

(a) Estimated from non-linear least squares fit of log-linear portion of disappearance curve following initial burst (see text).

Since the half-line of disappearance of free EGF was 1.0 hr, it is reasonable to assume that the release of EGF from the liposomes is the rate limiting step in the prolonged disappearance of EGF from the eye observed in liposome-containing formulations, and that observed disappearance half lives approximate half lives of EGF release from the liposomes From the first order rate equation:

$$A_t = A_0 * e^{-kt} \text{ or } \ln(A_t) = \ln(A_0) - kt$$

where k=0.693 / t$_{\frac{1}{2}}$, the amount of EGF lost from the eye during any day can be calculated. For example, the amount of EGF lost on day two (24–48 hrs) for Formulation I (k=0.049 hr $^{-1}$, A$_0$=85%) is founded by taking the difference between A$_{24}$ and A$_{48}$ where A$_{24}$=85 * e$^{-0.049*24}$=26.2 and A$_{48}$=85 * e$^{-0.049*48}$=8.09. This difference is 18.1% of the total dose administered.

Using the first-order rate constants from Table 2, and estimating A$_0$ as the total dose minus burst, the percentage of the administered EGF dose lost on each day was estimated (Table 3).

TABLE 5

|  | FORMULATION | | | |
|---|---|---|---|---|
|  | FREE EGF | I (No cholesterol) | II (entrapped) | III (adsorbed) |
| % Lost: (a) | | | | |
| Day 1 | 100 | 73.8 | 63.6 | 71.8 |
| Day 2 | 0 | 18.1 | 14.3 | 10.5 |
| Day 3 | 0 | 5.6 | 8.7 | 6.6 |
| Day 4 | 0 | 1.7 | 5.3 | 4.1 |
| Day 5 | 0 | 0.53 | 3.2 | 2.6 |
| Day 6 | 0 | 0.16 | 1.9 | 1.6 |

TABLE 5-continued

|  | FORMULATION | | | |
|---|---|---|---|---|
|  | FREE EGF | I (No cholesterol) | II (entrapped) | III (adsorbed) |
| Day 7 | 0 | 0.05 | 1.2 | 1.0 |

(a) Based on first order rate constants shown in Table 1 (see test for details of calculations). Day 1 values include initial burst. Values are % of total dose administered.

All three EGF/liposome compositions gave at least 1% per day for the first four days, and Composition II and III continued to deliver this amount of EGF for up to 7 days.

The addition of cholesterol reduced the rate of EGF disappearance in liposomes, but increased the initial burst release (up to 57% in the first 40 minutes). This burst effect may be due to release of adsorbed drug from the outer bilayer(s) during initial in vivo destabilization, but it is not clear why burst release was lower with the cholesterol free formulation (I). The effect of a burst release is to rapidly elevate local drug concentration after injection. Therefore, a certain degree of burst release may be advantageous in establishing rapid onset of action. Even though they lost more of their contents early, the cholesterolcontaining formulations (II and III) were able to deliver more drug on days 3 to 7 due to their slower release rate.

Local erythema and edema were observed in some rabbits following administration. All of the rabbits receiving free EGF displayed redness at 90 minutes and increasing edema by the end of the study (3 hours), at which time they were treated with ophthalmic ointment. Following injection of Formulation I, all eyes appeared reddened at 90 minutes, erythema and edema increasing to a maximum at 6 hours and then subsiding. Free EGF and Composition I contained Thimerosal and DTPA, and were not prepared aseptically. Composition II and III were subsequently prepared aseptically without Thimerosal or DTPA. These formulations caused mild erythema in 6 of 8 rabbits, but edema was observed in only one animal, indicating reduced irritation compared with the first two formulations.

Both Compositions II and III appeared to release EGF at approximately the same rate despite the fact that Composition II contained entrapped and absorbed drug while Composition III contained only adsorbed drug. This may indicate that EGF (an amphipathic peptide) is strongly adsorbed to the bilayer, as discussed in Example 3 above, and that the rate limiting step in its release involves desorption from its membrane associated state, rather than "leakage" through the lipid barrier.

Although specific embodiments and methods of making and using the invention have been described herein, it will be appreciated that various changes and modifications can be made without departing from the invention.

It is claimed:

1. A high-viscosity liposome composition for use in administering a sustained release dose of epidermal growth factor (EGF) at a wound or surgical incision site, comprising (a) EGF/liposomes (i) containing neutral phospholipid, between 10-50 weight percent negatively charged phospholipid, and liposome-entrapped EGF; and (ii) having a lipid concentration of at least 50 mg/g composition and a pH between 5.5 and 8.5; and (b) means for imparting a high composition viscosity selected from the group consisting of:
   (i) a low-conductivity aqueous medium containing a zwitterionic compound having an isoelectric point between pH 5.5 and 8.5; and
   (ii) empty liposomes which are substantially free of negatively charged phospholipid and entrapped EGF.

2. The composition of claim 1, wherein the neutral phospholipid is predominantly phophatidylcholine, and the negatively charged phospholipid is predominantly phophatidylglycerol.

3. The composition of claim 2, which contain at least about 25 mole percent of phosphatidylcholine, phosphatydylglycerol, and cholesterol.

4. The composition of claim 1, wherein the total concentration of liposomes in the composition is less than about 200 mg/g, and the aqueous medium is a conductivity medium containing a zwitterionic compound.

5. The composition of claim 5, wherein the zwitterionic compound is a neutral amino acid.

6. The composition of claim 5, wherein the concentration of zwitterionic compound is between 1–5 weight percent.

7. The composition of claim 6, wherein the concentration of the zwitterionic compound is adjusted to produce an substantially physiological osmolarity.

8. The composition of claim 1, wherein the high viscosity of the composition is produced by empty liposomes, the empty liposomes contain between about 20–50 mole percent cholesterol, and the total lipid concentration of both EGF/liposomes and empty liposomes in the composition is greater than about 400 mg/g composition.

9. The composition of claim 1, wherein the EGF is entrapped in the EGF/liposomes by surface adsorption to negatively charged liposomes.

10. The composition of claim 1, which is further characterized by a liposome size distribution in a selected size range less than about 2 microns.

11. An epidermal growth factor (EGF)/liposome composition having a gel-like consistency, comprising
(a) liposomes containing between 20–50 mole percent each of phosphatidylcholine, phosphatidylglycerol, and cholesterol, at a total lipid concentration of between about 50–200 mg/g composition;
(b) a low-conductivity aqueous medium containing a zwitterionic compound whose isoelectric point is between about pH 6–8; and
(c) liposome-entrapped EFG, at a concentration between about 0.5–5 μg/ml.

12. The composition of claim 11, wherein the phosphatidylcholine and phosphatidylglycerol are egg phosphatidylcholine and phosphatidylglycerol, respectively, and the zwitterionic compound is a neutral amino acid.

13. A method of forming an epidermal growth factor (EGF)/liposome composition having a gel-like consistency, comprising
(a) providing a lipid mixture containing neutral phospholipid, between 10–50 weight percent negatively charged phospholipid and EGF; and
(b) suspending (i) the lipid mixture to a final lipid concentration between about 50–200 mg/ml, and (ii) EGF, to a final EGF concentration of between about 0.1 and 10 μg/ml, in a low-conductivity aqueous medium containing a zwitterionic compound having an isoelectric point between pH 5.5–8.5.

14. The method of claim 13, wherein said mixing is carried out by adding said aqueous medium to a thin film of the lipid mixture in dried form.

15. The method of claim 14, which further includes extruding the composition through a defined-pore-size membrane which is effective to reduce the sizes of the liposomes in the composition to a selected size less than about 2 microns.

16. The method of claim 13, wherein said peptide is present in the aqueous medium at the time of liposome formation, to yield liposomes with encapsulated polypeptide.

17. The method of claim 13, wherein said peptide is added after formation of liposomes in the aqueous medium, and the polypeptide is predominantly adsorbed to the liposome surfaces.

18. The method of claim 13, wherein the aqueous medium initially is at a selected pH at which the zwitterionic compound is substantially charged, and which further includes rehydrating the lipid mixture at the selected pH, by said rehydrating, forming a relatively non-viscous suspension of liposomes, and adjusting the pH of the suspension to the isoelectric point of the zwitterionic compound, thereby to produce the gel-like composition.

19. The method of claim 18, wherein the lipid mixture is prepared by dehydrating a dispersion of liposomes which contain said zwitterionic compound in predominantly liposome encapsulated form, where the pH of the liposome suspension before dehydrating is such that mixing of the suspension with the aqueous medium produces, at equilibrium, a pH at which the zwitterionic compound is isoelectric, wherein adding said aqueous medium initially produces a liposome dispersion having such selected pH, and equilibration of the zwitterionic compound between inner and outer liposome spaces produces a final suspension pH at which the zwitterionic compound is isoelectric.

20. A method of treating a wound or surgical incision with a sustained release dose of epidermal growth factor (EGF),
providing a high-viscosity liposome composition comprising (a) EGF/liposomes (i) containing neutral phospholipid, at least about 10 weight percent negatively charged phospholipid, and liposome-entrapped EGF, and (ii) having a lipid concentration of less than about 200 mg/g composition and a pH between 5.5 and 8.5 and (b) means for imparting a high composition viscosity selected from the group consisting of (i) an low-conductivity aqueous medium containing a zwitterionic compound having an isoelectric point between 5.5 and 8.5; and (ii) empty liposomes which are substantially free of negatively charged phospholipid and liposome entrapped EGF, and
applying the composition to the wound or incision site.

21. The method of claim 20, wherein the liposomes contain between 25–50 mole percent each of egg phosphatidylcholine, egg phosphatidylglycerol, and cholesterol.

22. The method of claim 20, wherein the aqueous medium contains wherein the total concentration of liposomes in the composition is less than about 200 mg/g and the aqueous medium is a low-conductivity medium containing a zwitterionic compound.

23. The method of claim 22, wherein the pH of the composition is substantially at such isoelectric point.

24. The method of claim 23, wherein the zwitterionic compound is a neutral amino acid.

25. The method of claim 20, wherein the high viscosity of the composition is produced by empty liposomes, and the total lipid concentration of both EGF-/liposomes and empty liposomes in the composition is greater than about 400 mg/g composition.

26. The method of claim 20, wherein the amount of EGF released, over a several-day period, is at least about 1% per day of the total EGF originally present in the applied composition.

27. The method of claim 26, wherein the EGF is entrapped in the liposomes by surface adsorption.

28. The method of claim 20, for treatment of surface ulcers, wherein the composition is applied directly to the skin surface.

29. The method of claim 20, for treatment of surgical incision, wherein the composition is applied between surgical incision layers.

30. The method of claim 20, for treatment of ophthalmic surgical incisions involving both corneal and conjunctiva incisions, wherein the composition is injected to the space between the cornea and conjunctiva, after resuturing the conjunctiva.

* * * * *

UNITED STATES PATENT AND TRADEMARK OFFICE
CERTIFICATE OF CORRECTION

PATENT NO. : 4,944,948

DATED : July 31, 1990

INVENTOR(S) : Uster, P.; Fielding, R.; Martin, F.

It is certified that error appears in the above-identified patent and that said Letters Patent is hereby corrected as shown below:

In column 1, line 27 replace [26914 281] with --269-281--

In column 1, line 31 replace [O'3Keefe] with --O'Keefe--;

In column 4, line 3 delete [30];

In column 5, line 53 insert after involved --.--;

In column 9, line 36 replace [Studies] with --studies--;

In column 9, line 59 delete [14];

In column 12, line 27 replace [inciSion] with --incision--;

In column 18, line 68 replace [$1 \times 10^{-315}\%$] with --$1 \times 10^{-5}\%$--.

Signed and Sealed this

Nineteenth Day of November, 1991

*Attest:*

HARRY F. MANBECK, JR.

*Attesting Officer*  *Commissioner of Patents and Trademarks*